United States Patent
Liu et al.

(10) Patent No.: US 11,925,531 B2
(45) Date of Patent: Mar. 12, 2024

(54) MAGNETIC DRESSING AND PREPARATION METHOD AND USE THEREOF

(71) Applicant: SHANGHAI UNIVERSITY, Shanghai (CN)

(72) Inventors: Na Liu, Shanghai (CN); Ziheng Chen, Shanghai (CN); Huiyu Yuan, Shanghai (CN); Dan Zhang, Shanghai (CN); Kewei Zhang, Shanghai (CN); Tao Yue, Shanghai (CN); Yuanyuan Liu, Shanghai (CN); Yan Peng, Shanghai (CN)

(73) Assignee: Shanghai University, Shanghai (CN)

( * ) Notice: Subject to any disclaimer, the term of this patent is extended or adjusted under 35 U.S.C. 154(b) by 0 days.

(21) Appl. No.: 17/943,356

(22) Filed: Sep. 13, 2022

(65) Prior Publication Data
US 2023/0081314 A1 Mar. 16, 2023

(30) Foreign Application Priority Data
Sep. 15, 2021 (CN) .......................... 202111079086.8

(51) Int. Cl.
| | |
|---|---|
| *A61F 13/00* | (2006.01) |
| *A61F 13/02* | (2006.01) |
| *A61F 13/84* | (2006.01) |
| *A61L 15/18* | (2006.01) |
| *A61L 15/20* | (2006.01) |
| *A61L 15/44* | (2006.01) |
| *A61L 15/62* | (2006.01) |

(52) U.S. Cl.
CPC .. *A61F 13/00029* (2013.01); *A61F 13/00017* (2013.01); *A61F 13/00034* (2013.01); *A61F 13/0286* (2013.01); *A61L 15/18* (2013.01); *A61L 15/20* (2013.01); *A61L 15/44* (2013.01); *A61L 15/62* (2013.01); *A61F 2013/8479* (2013.01); *A61L 2300/41* (2013.01)

(58) Field of Classification Search
None
See application file for complete search history.

(56) References Cited

U.S. PATENT DOCUMENTS

2014/0288398 A1* 9/2014 Simberg ............... C12Q 1/6806
600/309

FOREIGN PATENT DOCUMENTS

| | | |
|---|---|---|
| CN | 102836288 A | 12/2012 |
| CN | 206566237 U | 10/2017 |
| CN | 110201038 A | 6/2019 |
| WO | WO-2006125074 A1 * | 11/2006 .......... A61K 9/0004 |

* cited by examiner

*Primary Examiner* — Robert A Wax
*Assistant Examiner* — Quanglong N Truong
(74) *Attorney, Agent, or Firm* — Bay State IP, LLC

(57) ABSTRACT

The present disclosure provides a magnetic dressing and a preparation method and use thereof, belonging to the technical field of pharmaceutical preparations. The magnetic dressing includes a magnetic layer, a drug-loading layer, and a protective layer that are stacked in sequence, where the magnetic layer includes polyvinyl alcohol, gluten, and iron particles. In the present disclosure, a swallowed magnetic dressing is controlled by an external magnetic field, and the magnetic dressing is moved to a pathological position by changing a direction of the external magnetic field; after the external magnetic field is removed, the magnetic dressing changes from a ring to a sheet, thereby completing attachment of an entire lesion surface to complete treatment by autonomous drug release.

19 Claims, 4 Drawing Sheets

MAGNETIC DRESSING AND PREPARATION METHOD AND USE THEREOF

CROSS REFERENCE TO RELATED APPLICATION

This patent application claims the benefit of and takes priority from Chinese Patent Application No. 202111079086.8, filed on Sep. 15, 2021, the disclosure of which is incorporated by reference herein in its entirety as part of the present application.

TECHNICAL FIELD

The present disclosure relates to the technical field of pharmaceutical preparations, in particular to a magnetic dressing and a preparation method and use thereof.

BACKGROUND ART

Due to an increasingly rapid pace of life in modern society, people's study and work are under great pressure and intensity. These factors cause frequently irregular diet, non-timing diet, and eating less during busyness and overeating during leisure, leading to the deterioration of gastric ulcers into gastric perforation. In recent years, researches on micro-nano robots have become increasingly popular, and micro-nano robots with different manufacturing processes and structures have been developed. These micro-nano robots are widely used in many fields, such as drug targeted delivery, cell capture and isolation, and 3D tissue assembly. Meanwhile, with the continuous deepening of researches, control methods are also increasingly developed for movement of the micro-nano robots. According to driving mechanisms, the control methods mainly include two types: I, chemical driving, providing a driving force for the movement of micro-nano robots through the redox reaction of fuels; II, external field driving, generally realizing navigation motion of the micro-nano robots using eternal physical fields, such as a magnetic field, an electric field, a sound field, and an optical field. Magnetic field driving has desirable biocompatibility, biopenetrability, and high control accuracy, and can accurately drive the micro-nano robots to reach pathological positions to complete targeted therapy; the magnetic field driving has shown a great potential for use in the field of in vivo targeted therapy.

Although the drug loading/delivery method of magnetically driven micro-nano robots is becoming more and more mature, the treatment method mainly realizes targeted therapy through a diffusion effect of drugs. During the drug release of the micro-nano robots, the released drugs do not have direct contact with the lesions; when faced with inflammation of the lining of certain organs or gastric perforation, there may be a lower efficacy.

SUMMARY

In view of this, an objective of the present disclosure is to provide a magnetic dressing and a preparation method and use thereof. The magnetic dressing can realize fixed-point release of a drug, thereby improving a therapeutic effect of the drug.

To achieve the above objective, the present disclosure provides the following technical solutions.

The present disclosure provides a magnetic dressing, including a magnetic layer, a drug-loading layer, and a protective layer that are stacked in sequence, where the magnetic layer includes polyvinyl alcohol, gluten, and iron particles.

Preferably, the gluten, the iron particles, and the polyvinyl alcohol may have a mass ratio of 1:8:1.1.

Preferably, the iron particles may have a particle size of 6 μm to 10 μm.

Preferably, the protective layer may be prepared by a cross-linking reaction of sodium alginate and calcium chloride.

Preferably, the drug-loading layer may be a hydrogel prepared from chitosan and an anti-inflammatory drug.

The present disclosure further provides a preparation method of the magnetic dressing, including the following steps:

preparing the drug-loading layer;

spraying a magnetic layer slurry including the polyvinyl alcohol, the gluten, and the iron particles on a surface of the drug-loading layer to form the magnetic layer, thereby obtaining a double-layer dressing; and forming the protective layer on a surface of the double-layer dressing to obtain the magnetic dressing.

Preferably, the drug-loading layer may be prepared by: mixing the chitosan and the anti-inflammatory drug at a mass ratio of 1:1 with water to obtain the hydrogel.

Preferably, the preparation method may further include conducting magnetization at a magnetic flux density of 10 mT to 20 mT after forming the magnetic layer.

Preferably, the protective layer may be formed by: dipping the double-layer dressing in a sodium alginate solution and a calcium chloride solution in sequence; the sodium alginate solution may have a mass fraction of 6%, and the calcium chloride solution may have a mass fraction of 4%; and the sodium alginate solution and the calcium chloride solution may have a mass ratio of 1:1.

The present disclosure further provides use of the magnetic dressing or a magnetic dressing prepared by the preparation method in preparation of a targeted drug.

The present disclosure provides a magnetic dressing, including a magnetic layer, a drug-loading layer, and a protective layer that are stacked in sequence, where the magnetic layer includes polyvinyl alcohol, gluten, and iron particles. In the present disclosure, a swallowed magnetic dressing is controlled by an external magnetic field, and the magnetic dressing is moved to a pathological position by changing a direction of the external magnetic field; after the external magnetic field is removed, the magnetic dressing changes from a ring to a sheet, thereby completing attachment of an entire lesion surface to complete treatment by autonomous drug release.

Beneficial Effects

The magnetic dressing includes a magnetic layer, a drug-loading layer, and a protective layer, where the drug-loading layer can be replaced according to different pathological states to achieve sustainable medical treatment; the protective layer can prevent the magnetic dressing from being eroded by the internal environment of the living body during exercise, resulting in a decrease in efficacy; driven by an external magnetic field, the magnetic dressing accurately reaches the lesions in different motion modes, realizing a method similar to the plaster sticking treatment, and realizing the fixed-point release of drugs, thereby improving a therapeutic effect of the drugs; the magnetic dressing appears in a ring shape under an action of the external magnetic field, and then in a sheet shape when the magnetic field is removed; the ring shape provides a possibility for the drugs to enter the human body by swallowing, and the sheet shape enables the drugs to be attached to a gastric perforation site to achieve precisely-targeted drug release therapy; and the magnetic dressing has a simple operation and a low cost.

Further, the raw materials of the magnetic dressing are biodegradable materials; after the magnetic dressing is removed from affected parts, a permanent magnet can be removed to terminate the treatment; and the magnetic dressing can be naturally degraded in the human body.

Further, the protective layer is prepared by a cross-linking reaction of sodium alginate and calcium chloride; a pore structure of the protective layer changes with a physiological environment of the target site. When being in contact with the lesion, the pore structure becomes larger to release the drugs; as the lesion site gradually shrinks, the pore structure shrinks at a position in contact with the recovery site, gradually reducing the release of the drugs, to realize a controlled release of the drugs on demand.

The present disclosure further provides a preparation method of the magnetic dressing, including the following steps: preparing the drug-loading layer; spraying a magnetic layer slurry including the polyvinyl alcohol, the gluten, and the iron particles on a surface of the drug-loading layer to form the magnetic layer, thereby obtaining a double-layer dressing; and forming the protective layer on a surface of the double-layer dressing to obtain the magnetic dressing.

DETAILED DESCRIPTION OF THE EMBODIMENTS

The present disclosure provides a magnetic dressing, including a magnetic layer, a drug-loading layer, and a protective layer that are stacked in sequence, where the magnetic layer includes polyvinyl alcohol, gluten, and iron particles.

In the present disclosure, the gluten, the iron particles, and the polyvinyl alcohol have a mass ratio of preferably 1:8:1.1. The polyvinyl alcohol has desirable biocompatibility. The polyvinyl alcohol is preferably added in the form of a polyvinyl alcohol solution with a mass fraction of 10%.

In the present disclosure, the iron particles have a particle diameter of preferably 6 μm to 10 μm.

In the present disclosure, the magnetic layer acts as a driving layer, and is a key to deformation and movement of the magnetic dressing under the action of an external magnetic field.

In the present disclosure, the protective layer is prepared preferably by a cross-linking reaction of sodium alginate and calcium chloride. A main function of the protective layer is to prevent the drug-loading layer from reacting in different physiological environments during the movement of the magnetic dressing in the living body, resulting in the leakage of the drug and causing side effects on other tissues and organs.

In the present disclosure, the protective layer prepared by the cross-linking reaction of the sodium alginate and the calcium chloride does not react in an acidic environment, but dissolves in an alkaline environment.

In the present disclosure, the protective layer has a thickness of preferably 800 μm to 1,000 μm.

In the present disclosure, the drug-loading layer is preferably a hydrogel prepared from chitosan and an anti-inflammatory drug. The drug-loading layer is a storage drug-loading layer, and different drug-loading layers can be prepared for different diseases.

In the present disclosure, the chitosan and the anti-inflammatory drug have a mass ratio of preferably 1:1. The chitosan has outstanding biocompatibility, biodegradability, antibacterial properties, anticorrosion, hemostasis, and wound healing promotion.

In the present disclosure, the anti-inflammatory drug is preferably bismuth potassium citrate; the potassium bismuth citrate can promote the regeneration of gastric mucosa, such that the gastric mucosa is protected to a certain extent, and the disease symptoms of gastric ulcers can be alleviated.

In the present disclosure, the magnetic dressing has a magnetic flux density of preferably 10 mT to 20 mT (measured by a Gauss meter).

Figure 1:
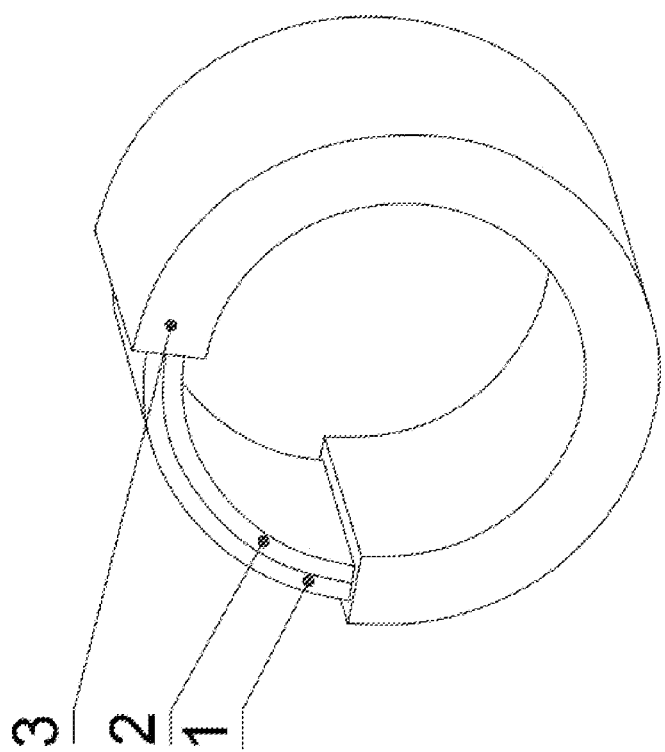
FIG. 1 shows a state of the magnetic dressing of the present disclosure when an external magnetic field is applied, where 1 is a drug-loading layer, 2 is a magnetic layer, and 3 is a protective layer.
Figure 2:
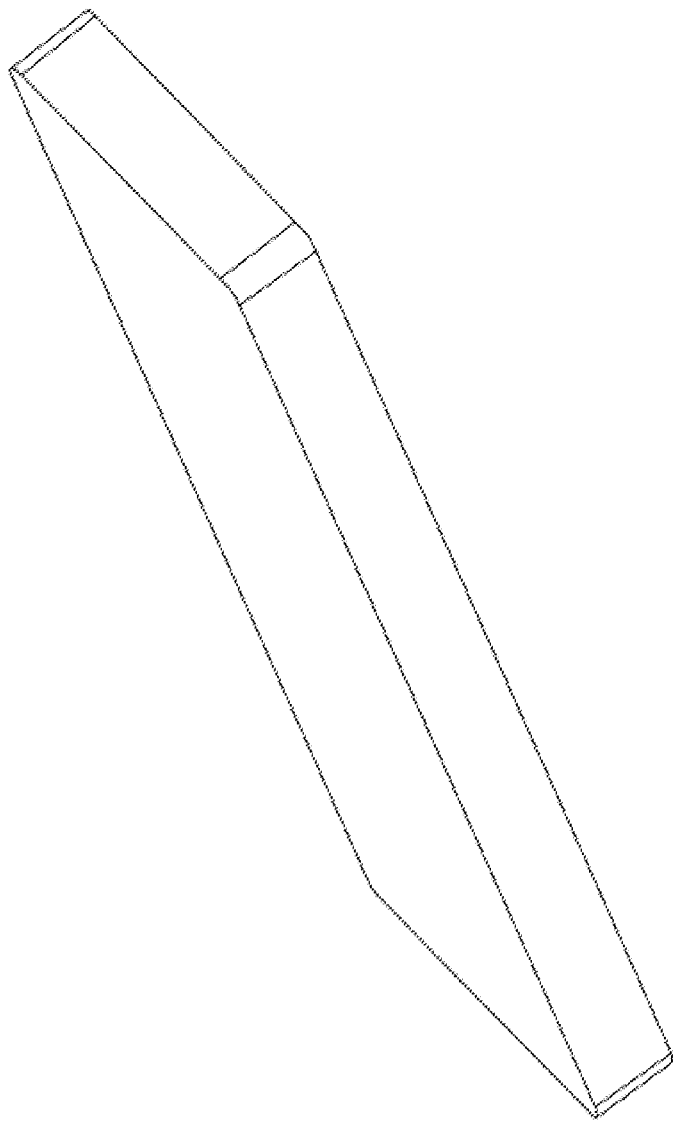
FIG. 2 shows a state of the magnetic dressing of the present disclosure when an external magnetic field is not applied.
Figure 3:
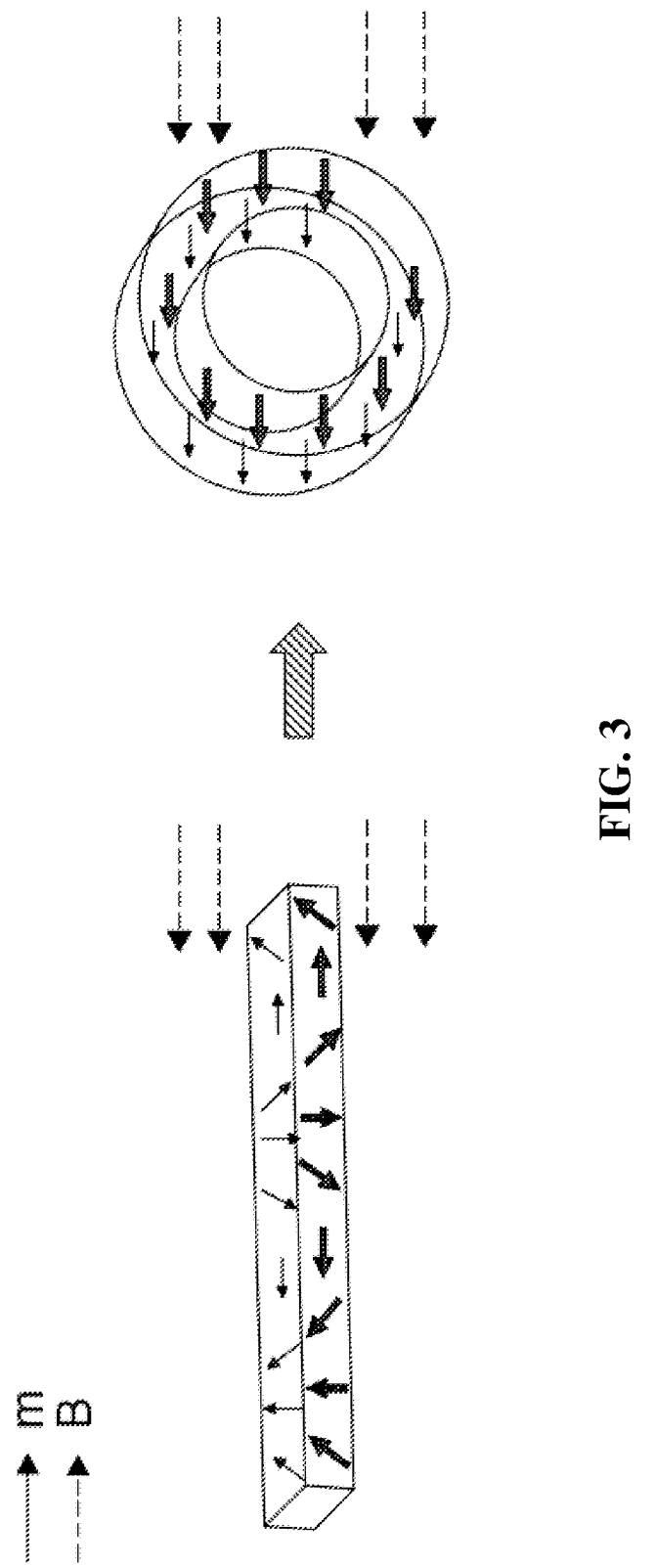
FIG. 3 shows a deformation principle of the magnetic layer of the magnetic dressing of the present disclosure.
Figure 4:
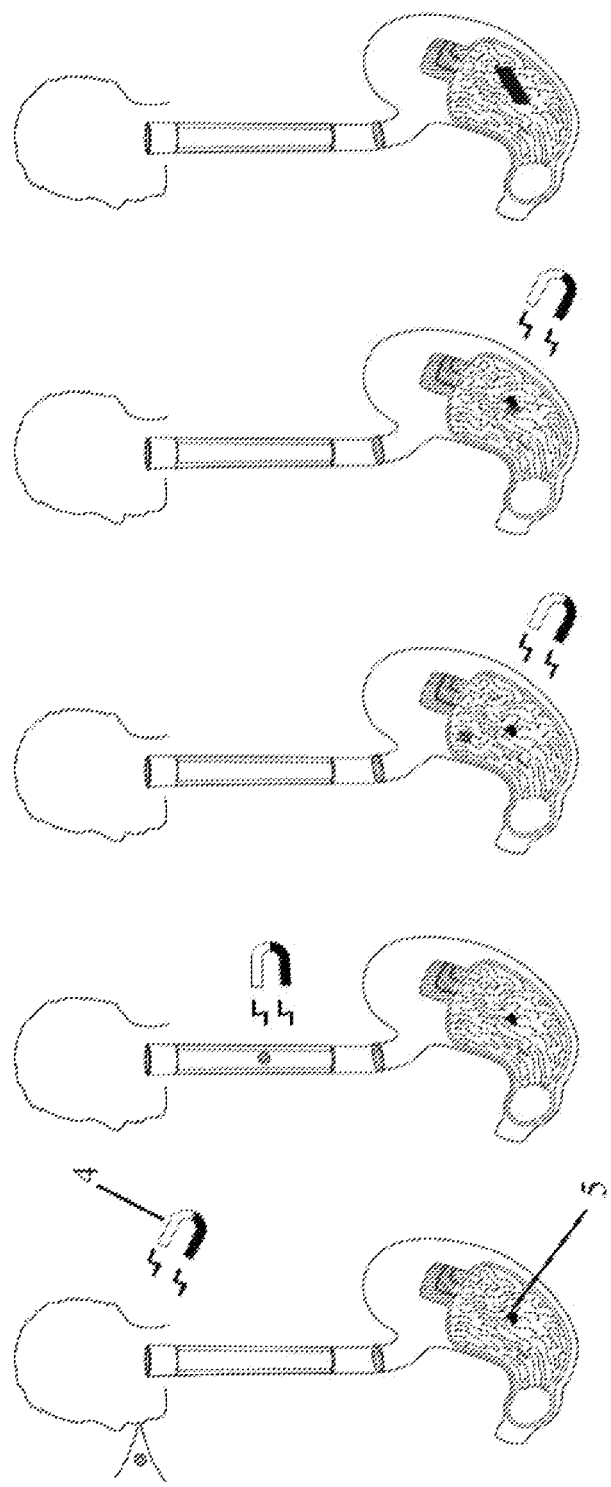
FIG. 4 shows a flow chart of a targeted therapy using the magnetic dressing of the present disclosure, where 4 is a permanent magnet, and 5 is a lesion.

FIG. 1 shows a state of the magnetic dressing of the present disclosure when an external magnetic field is applied, where 1 is a drug-loading layer, 2 is a magnetic layer, and 3 is a protective layer; and FIG. 2 shows a state of the magnetic dressing of the present disclosure when an external magnetic field is not applied. FIG. 3 shows a deformation principle of the magnetic layer of the magnetic dressing of the present disclosure; and FIG. 4 shows a flow chart of a targeted therapy using the magnetic dressing of the present disclosure, where 4 is a permanent magnet, and 5 is a lesion.

In the present disclosure, under a magnetic field applied by a permanent magnet, the magnetic dressing appears as a ring shape, as shown in formulas [1] and [2]:

$$M_{net} = \int_0^L RmAds \quad [1]$$

$$\tau = M_{net} \times B \quad [2]$$

In the formula, m a magnetization intensity curve; R is a rotation matrix; A is a cross-sectional area; L is a length of the magnetic dressing, $M_{net}$ is a net magnetic moment, and when no deformation occurs, the magnetic dressing has no net magnetic moment; B is a magnetic flux density of an external magnetic field, and τ is a magnetic torque generated by the external magnetic field. When an external magnetic field is applied, the magnetic layer 2 is bent and deformed to generate a net magnetic moment. The net magnetic moment and the external magnetic field generate a magnetic torque. The magnetic dressing is bent under the action of the magnetic torque until the net magnetic moment is consistent with the direction of the magnetic flux density of the external magnetic field. The bending stops, forming a ring-shaped magnetic dressing.

The patient allows the ring-shaped magnetic dressing to enter the human body by swallowing, and then the ring-shaped magnetic dressing moves to the lesion 5 under the control of the permanent magnet 4 and comes into contact with the lesion 5. The permanent magnet 4 is slowly removed, the magnetic dressing is slowly deformed to form a sheet shape, and the drug-loading layer of the magnetic dressing is closely attached to an affected part, and then releases drugs to the affected part in the next period of time to implement precisely targeted therapy. After the therapy is completed, a magnetic torque: is applied to the magnetic dressing again using the permanent magnet, such that the magnetic dressing is deformed into a ring shape and falls off the affected part.

The present disclosure further provides a preparation method of the magnetic dressing, including the following steps:

preparing the drug-loading layer;

spraying a magnetic layer slurry including the polyvinyl alcohol, the gluten, and the iron particles on a surface of the drug-loading layer to form the magnetic layer, thereby obtaining a double-layer dressing; and forming the protective layer on a surface of the double-layer dressing to obtain the magnetic dressing.

In the present disclosure, the drug-loading layer is prepared.

In the present disclosure, the drug-loading layer is prepared preferably by: mixing the chitosan and the anti-inflammatory drug at a mass ratio of preferably 1:1 with water to obtain the hydrogel. The specific limitation of the anti-inflammatory drug is preferably the same as the above scheme, and will not be repeated here.

In the present disclosure, the magnetic layer slurry including the polyvinyl alcohol, the gluten, and the iron particles is sprayed on the surface of the drug-loading layer to form the magnetic layer, thereby obtaining the double-layer dressing. The specific limitation of consumption and particle size of the polyvinyl alcohol, the gluten, and the iron particles each are preferably consistent with the above scheme, and will not be repeated here.

In the present disclosure, the spraying is conducted at a thickness of preferably 1 mm to 2 mm.

In the present disclosure, after the spraying, the method includes preferably curing; there is no special limitation on a specific method of the curing, and methods well known to those skilled in the art can be used.

In the present disclosure, after the magnet layer is formed, preferably the magnetic layer is on an inner side and the drug-loading layer is on an outer side, which are bent on a cylindrical surface, and magnetization is conducted to obtain a double-layer dressing.

In the present disclosure, the magnetization has a magnetic flux density of preferably 10 mT to 20 mT. The magnetization is conducted preferably using a magnetizer with a magnetic flux density of preferably 2.5 T to 3 T. The magnetization enables the magnetic layer to have a specific magnetization curve, facilitating swallowing and delivery of the dressing.

In the present disclosure, the double-layer dressing is dipped in a protective layer slurry to form the protective layer to obtain the magnetic dressing.

In the present disclosure, the protective layer slurry is preferably prepared by mixing a sodium alginate solution and a calcium chloride solution; the sodium alginate solution has a mass fraction of preferably 6%, and the calcium chloride solution has a mass fraction of preferably 4%; and the sodium alginate solution and the calcium chloride solution have mass ratio preferably 1:1.

The present disclosure further provides use of the magnetic dressing or a magnetic dressing prepared by the preparation method in preparation of a targeted drug. There is no special limitation on a specific manner of the use, and manners well known to those skilled in the art can be used.

In the present disclosure, the use includes preferably targeted therapy of pathological positions during gastric ulcers and accelerated wound healing after gastric perforation surgery.

In the present disclosure, a method for realizing the precise targeted therapy in vivo by the magnetic dressing specifically includes the following steps:

a. Magnetic dressing preparation: the magnetic dressing to be used is prepared in advance before the treatment, in a sheet form.

b. A magnetic torque is applied to the magnetic dressing through a permanent magnet, and the magnetic dressing is deformed into a ring shape under an action of the magnetic torque. At this time, the protective layer is on the outside, and the magnetic layer is on the inside.

c. A patient ingests the ring-shaped magnetic dressing into the stomach by swallowing.

d. The ring-shaped magnetic dressing is moved to an affected part of the patient's stomach through the permanent magnet, and then closely attached to the affected part.

e. The permanent magnet is removed, that is, the magnetic torque is removed; the magnetic dressing slowly recovers into a sheet; during this process, since the magnetic dressing has a strong adhesion, the protective layer of the magnetic dressing is always closely attached to the affected part.

f. The protective layer of the magnetic dressing is degraded under a special physiological environment of the inflammatory site, and the drug-loading layer is exposed to release the drugs to the affected part to achieve precise treatment.

g. After the treatment, the magnetic torque is applied to the magnetic dressing again through the permanent magnet, such that the magnetic dressing is deformed into a ring shape and falls off the affected part.

h. According to actual needs, the above steps can be repeated to achieve targeted and precise treatment of multiple drugs at the same site until the end of the entire treatment. The magnetic dressing is prepared by biodegradable materials; after the magnetic dressing is removed from affected parts, a permanent magnet can be removed to terminate the treatment; and the magnetic dressing can be naturally degraded in the human body.

To further explain the present disclosure, the magnetic dressing and the preparation method and the use thereof provided in the present disclosure will be described in detail below in conjunction with examples which, however, should not be interpreted as limitations to the protection scope of the present disclosure.

Example 1

A hydrogel was prepared by chitosan and potassium bismuth citrate in a mass ratio of 1:1 as a drug-loading layer, gluten, iron particles, and polyvinyl alcohol solution (mass fraction 10%) had a mass ratio of 1:8:11, and the iron particles had a particle size of 6 μm; the gluten, the iron particles, and a polyvinyl alcohol solution were mixed to obtain a magnetic layer slurry; the magnetic layer slurry was sprayed on a surface of the drug-loading layer with a thickness of 100 μm, and then cured to form a cured dressing; the cured dressing was bent onto a cylindrical surface, with the magnetic layer on an inside and the drug-loading layer on an outside, and magnetized (at a magnetic flux density of 10 mT) to obtain a double-layer dressing; the double-layer dressing was put into a sodium alginate solution (with a mass fraction 6%), and then transferred into a calcium chloride solution (with a mass fraction 4%), where the sodium alginate solution and the calcium chloride solution had a mass ratio of 1:1; the sodium alginate and the calcium chloride was subjected to a cross-linking reaction to encapsulate the surface of the double-layer dressing, to form a calcium alginate hydrogel protective layer that did not react in an acidic environment but dissolved in an alkaline environment, thereby forming a magnetic dressing.

A method for realizing the precise targeted therapy in vivo by the magnetic dressing specifically included the following steps:

a. Magnetic dressing preparation.

b. A magnetic torque was applied to the magnetic dressing through a permanent magnet, and the magnetic dressing was deformed into a ring shape under an action of the magnetic torque. At this time, the protective layer was on the outside, and the magnetic layer was on the inside.

c. A patient ingested the ring-shaped magnetic dressing into the stomach by swallowing.

d. The ring-shaped magnetic dressing was moved to an affected part of the patient's stomach through the permanent magnet, and then closely attached to the affected part.

e. The permanent magnet was removed, that is, the magnetic torque was removed; the magnetic dressing slowly recovered into a sheet; during this process, since the magnetic dressing had a strong adhesion, the protective layer of the magnetic dressing was always closely attached to the affected part.

f. The protective layer of the magnetic dressing was degraded under a special physiological environment of the inflammatory site, and the drug-loading layer was exposed to release the drugs to the affected part to achieve precise treatment.

g. After the treatment, the magnetic torque was applied to the magnetic dressing again through the permanent magnet, such that the magnetic dressing was deformed into a ring shape and fell off the affected part.

h. According to actual needs, the above steps could be repeated to achieve targeted and precise treatment of multiple drugs at the same site until the end of the entire treatment. The magnetic dressing was prepared by biodegradable materials; after the magnetic dressing was removed from affected parts, a permanent magnet could be removed to terminate the treatment; and the magnetic dressing could be naturally degraded in the human body.

The above described are merely preferred implementations of the present disclosure rather than limitations to the present disclosure in any form. It should be noted that those of ordinary skill in the art may further make several improvements and modifications without departing from the principle of the present disclosure, but such improvements and modifications should be deemed as falling within the protection scope of the present disclosure.

What is claimed is:

1. A magnetic dressing configured for targeted therapy, comprising: a magnetic layer, a drug-loading layer, and a protective layer that are stacked in sequence, wherein the magnetic layer comprises polyvinyl alcohol, gluten, and iron particles; a swallowed magnetic dressing is controlled by an external magnetic field, and the magnetic dressing is moved to a pathological position by changing a direction of the external magnetic field, thereby achieving a fixed-point release of a drug; the magnetic dressing appears a ring shape under an action of the external magnetic field, and the ring shape makes the magnetic dressing enter the human body by swallowing; after removing the external magnetic field, the magnetic dressing changes from the ring shape to a sheet shape, completing attachment of an entire lesion surface to complete a treatment by conducting autonomous drug release; the magnetic layer as an inner side and the drug-loading layer as an outer side are bent on a cylindrical surface, and magnetization is conducted; and the magnetization enables the magnetic layer to have a specific magnetization curve, enabling swallowing and delivery of the dressing, wherein raw materials of the magnetic dressing are biodegradable and after the magnetic dressing is removed from the affected parts a permanent magnet is removed to terminate the treatment, and wherein the magnetic dressing is naturally degraded in the human body.

2. The magnetic dressing according to claim 1, wherein the gluten, the iron particles, and the polyvinyl alcohol have a mass ratio of 1:8:1.1.

3. The magnetic dressing according to claim 1, wherein the iron particles have a particle size of 6 μm to 10 μm.

4. The magnetic dressing according to claim 2, wherein the iron particles have a particle size of 6 μm to 10 μm.

5. The magnetic dressing according to claim 1, wherein the protective layer is prepared by a cross-linking reaction of sodium alginate and calcium chloride.

6. The magnetic dressing according to claim 1, wherein the drug-loading layer is a hydrogel prepared from chitosan and an anti-inflammatory drug.

7. A preparation method of the magnetic dressing according to claim 1, comprising the following steps:
preparing the drug-loading layer;
spraying a magnetic layer slurry comprising the polyvinyl alcohol, the gluten, and the iron particles on a surface of the drug-loading layer to form the magnetic layer, thereby obtaining a double-layer dressing; and
forming the protective layer on a surface of the double-layer dressing to obtain the magnetic dressing.

8. The preparation method according to claim 7, wherein the gluten, the iron particles, and the polyvinyl alcohol have a mass ratio of 1:8:1.1.

9. The preparation method according to claim 7, wherein the iron particles have a particle size of 6 μm to 10 μm.

10. The preparation method according to claim 8, wherein the iron particles have a particle size of 6 μm to 10 μm.

11. The preparation method according to claim 7, wherein the protective layer is prepared by a cross-linking reaction of sodium alginate and calcium chloride.

12. The preparation method according to claim 7, wherein the drug-loading layer is a hydrogel prepared from chitosan and an anti-inflammatory drug.

13. The preparation method according to claim 7, wherein the drug-loading layer is prepared by: mixing the chitosan and the anti-inflammatory drug at a mass ratio of 1:1 with water to obtain the hydrogel.

14. The preparation method according to claim 8, wherein the drug-loading layer is prepared by: mixing the chitosan and the anti-inflammatory drug at a mass ratio of 1:1 with water to obtain the hydrogel.

15. The preparation method according to claim 9, wherein the drug-loading layer is prepared by: mixing the chitosan and the anti-inflammatory drug at a mass ratio of 1:1 with water to obtain the hydrogel.

16. The preparation method according to claim 10, wherein the drug-loading layer is prepared by: mixing the chitosan and the anti-inflammatory drug at a mass ratio of 1:1 with water to obtain the hydrogel.

17. The preparation method according to claim 11, wherein the drug-loading layer is prepared by: mixing the chitosan and the anti-inflammatory drug at a mass ratio of 1:1 with water to obtain the hydrogel.

18. The preparation method according to claim 7, further comprising conducting magnetization at a magnetic flux density of 10 mT to 20 mT after forming the magnetic layer.

19. The preparation method according to claim 7, wherein the protective layer is formed by: dipping the double-layer dressing in a sodium alginate solution and a calcium chloride solution in sequence; the sodium alginate solution has a mass fraction of 6%, and the calcium chloride solution has a mass fraction of 4%; and the sodium alginate solution and the calcium chloride solution have a mass ratio of 1:1.

\* \* \* \* \*